United States Patent
Hvidtfeldt et al.

(10) Patent No.: US 6,880,384 B2
(45) Date of Patent: Apr. 19, 2005

(54) BLOOD ANALYZER, BLOOD SAMPLE HANDLER, AND METHOD FOR HANDLING A BLOOD SAMPLE

(75) Inventors: Kristian Jacob Hvidtfeldt, Virum (DK); Flemming Aas, Søborg (DK); Caspar Buchholtz Frederiksen, Tikøb (DK); Erik Kjølbye Hansen, Søborg (DK)

(73) Assignee: Radiometer Medical A/S, Bronshoj (DK)

( * ) Notice: Subject to any disclaimer, the term of this patent is extended or adjusted under 35 U.S.C. 154(b) by 0 days.

(21) Appl. No.: 10/327,838

(22) Filed: Dec. 23, 2002

(65) Prior Publication Data

US 2003/0126914 A1 Jul. 10, 2003

Related U.S. Application Data

(63) Continuation-in-part of application No. 10/184,678, filed on Jun. 26, 2002, now abandoned.

(30) Foreign Application Priority Data

Jun. 26, 2001 (DK) .......................................... 2001 00995

(51) Int. Cl.$^7$ .......................... G01N 1/00; G01N 33/48; B01F 13/08
(52) U.S. Cl. ....................... 73/64.56; 73/53.01; 422/50; 422/63; 422/68.1; 422/99
(58) Field of Search .............................. 73/53.01, 64.56; 422/44, 50, 63, 68.1, 99; 366/241, 242, 244, 273, 274

(56) References Cited

U.S. PATENT DOCUMENTS

| | | | |
|---|---|---|---|
| 3,967,934 A | * | 7/1976 | Seitz et al. ................. 73/54.15 |
| 4,081,242 A | * | 3/1978 | Girolami .................... 73/54.01 |
| 4,116,564 A | * | 9/1978 | Renaud et al. ............. 73/64.43 |
| 4,214,874 A | | 7/1980 | White ......................... 422/100 |
| 4,441,510 A | | 4/1984 | Worley, deceased et al. .... 600/576 |
| 4,475,411 A | | 10/1984 | Wellerfors |
| 4,609,017 A | | 9/1986 | Coulter et al. |
| 5,227,138 A | | 7/1993 | Boyd et al. .................. 422/102 |
| 5,248,480 A | * | 9/1993 | Greenfield et al. ......... 422/68.1 |
| 5,352,036 A | | 10/1994 | Haber et al. .................. 422/72 |
| 5,366,896 A | | 11/1994 | Margrey et al. |
| 5,750,440 A | * | 5/1998 | Vanell et al. ............... 438/692 |
| 5,959,221 A | | 9/1999 | Boyd et al. |
| 6,258,323 B1 | | 7/2001 | Hormann et al. ............. 422/99 |
| 6,382,827 B1 | | 5/2002 | Gebrian ....................... 366/274 |
| 6,467,946 B1 | * | 10/2002 | Gebrian ....................... 366/273 |
| 2002/0182110 A1 | | 12/2002 | Behnk ......................... 366/130 |

FOREIGN PATENT DOCUMENTS

| | | |
|---|---|---|
| EP | 0 295 048 A2 | 12/1988 |
| WO | WO 00/12157 | 3/2000 |

* cited by examiner

Primary Examiner—Daniel S. Larkin
(74) Attorney, Agent, or Firm—Bryan Cave LLP

(57) ABSTRACT

A blood analyzer has a control system controlling the operation of the analyzer, a sensor measuring a parameter of a blood sample, exposure means exposing the sensor to the blood sample, reporting means reporting the parameter of the blood sample, and a sample handler. The sample handler comprises a sampler bed receiving a blood sampler which contains the blood sample and a stirring element. The sample handler further comprises moving means moving the stirring element in the blood sampler when the sampler is arranged in the sampler bed. The blood analyzer is capable of handling and analyzing blood samples. A blood sample handler is provided as well, as are methods for handling and analyzing of a blood sample. The moving means moving the stirring element is preferably a magnet and the stirring element is magnetic.

31 Claims, 8 Drawing Sheets

US 6,880,384 B2

BLOOD ANALYZER, BLOOD SAMPLE HANDLER, AND METHOD FOR HANDLING A BLOOD SAMPLE

This is a Continuation-In-Part of application Ser. No. 10/184,678, filed Jun. 26, 2002 now abandoned.

FIELD OF THE INVENTION

The present invention relates to a blood analyzer, a method for handling and analyzing a blood sample, a blood sample handler, and a method for handling a blood sample.

BACKGROUND OF THE INVENTION

In the evaluation of the condition of a critically ill patient, blood analysis plays a key role. Blood analysis may include the measurement of blood gas parameters like pH, $PO_2$, $pCO_2$, metabolic parameters like glucose and lactate, and electrolytes like sodium, potassium and chloride.

The analytic process of blood analysis, and in particular blood gas analysis, is an integrated process including the preanalytical phase, the analytical phase and the postanalytical phase. In order to obtain correct results from the analysis, proper handling of samples and data should be ensured in each of these phases.

Prior to analysis, a blood sample may coagulate or settle or the sample may react with air in the blood sampler. In particular for blood gas analysis, the presence of air bubbles may bias the results and should be avoided. Often, an anticoagulant is added to the blood sample, and the sample is thoroughly stirred before analysis. The purpose of the stirring of blood samples is at least two-fold: It facilitates the dissolution of anticoagulant, e.g. heparin, added to the blood sample, and it prevents settling. Failure to properly dissolve the heparin may lead to formation of micro clots, which in turn may bias results and/or damage the analyzer. Settling may lead to sample inhomogeneity and misleading analytical results.

Traditionally, sample maintenance by stirring of samples for blood analysis is done manually by repeatedly inverting the sampler and by rolling it horizontally. A stirring element may be introduced into the sampler to improve stirring when shifted back and forth in the sampler. In this way, stirring is done without introducing any air into the sampler.

An example of an integrated analytical system for blood analysis is disclosed in U.S. Pat. No. 5,366,896. U.S. Pat. No. 5,366,896 discloses an integrated analytical system with a plurality of remote laboratories and a central monitoring station for the analysis of blood samples. The system includes a sample storage rack in which a plurality of blood sample containing syringes may be arranged and rotated for sample maintenance. Subsequent to rotation, syringes are automatically transferred to an analysis section of the analytical system for sample analysis. The rotational mixing disclosed in U.S. Pat. No. 5,366,896, however, is insufficient to ensure homogeneity of a blood sample.

Thus, despite the hitherto proposed blood analyzers, there is still a need for a blood analyzer which provides handling and analysis of blood samples for blood analysis. Further, there is a need for a sample handler providing handling of blood samples for blood analysis.

SUMMARY OF THE INVENTION

Thus, according to a first aspect of the invention a blood analyzer is provided which comprises:

a control system controlling the operation of the analyzer;

a sensor measuring a parameter of a blood sample;

exposure means exposing the sensor to the blood sample;

reporting means reporting the parameter of the blood sample; and a sample handler comprising:
  a sampler bed receiving a blood sampler which contains the blood sample and a stirring element, and
  moving means moving the stirring element in the sampler when the sampler is arranged in the sampler bed.

According to a second aspect of the invention, a method for handling and analyzing a blood sample contained in a blood sampler with a stirring element is provided, said method comprising the steps of:

arranging the blood sampler in a sampler bed in a sample handler of a blood analyzer;

stirring the blood sample by moving the stirring element in the sampler;

exposing the sensor to the blood sample;

measuring a parameter of the blood sample; and reporting the parameter.

According to a third aspect of the invention, a blood sample handler is provided which comprises:

an interface providing operational communication with a blood analyzer, a sampler bed receiving a blood sampler which contains a blood sample and a stirring element, and moving means moving the stirring element in the sampler when the sampler is arranged in the sampler bed.

According a fourth aspect of the invention, a method for handling a blood sample contained in a blood sampler with a stirring element is provided, comprising the steps of:

arranging the blood sampler in a sampler bed in a sample handler; and stirring the blood sample by moving the stirring element in the sampler.

DETAILED DESCRIPTION OF THE INVENTION

Figure 1:
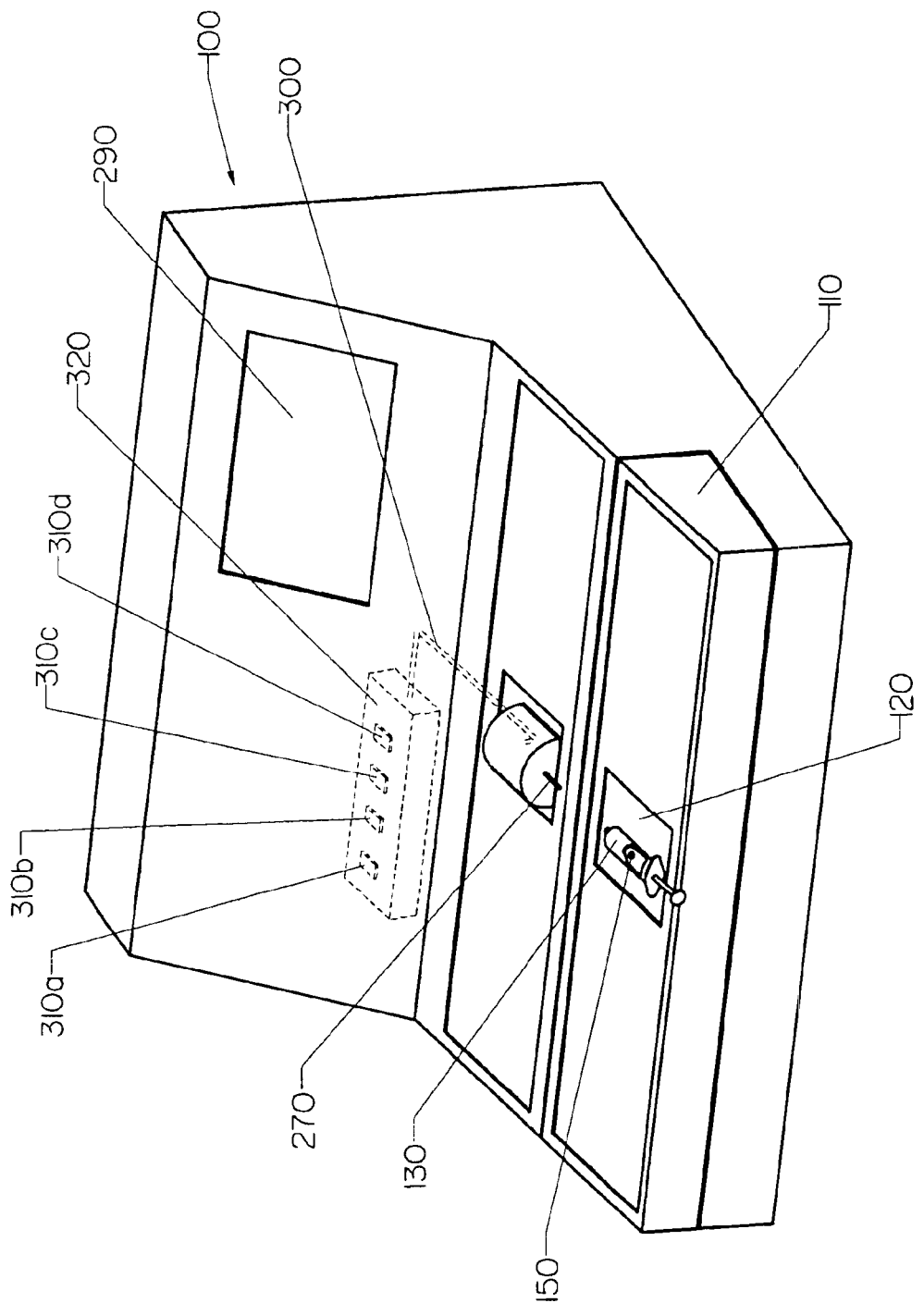
FIG. 1 shows an embodiment of a blood analyzer according to the invention.

According to a first aspect of the invention a blood analyzer is provided which comprises:

a control system controlling the operation of the analyzer;

a sensor measuring a parameter of a blood sample;

exposure means exposing the sensor to the blood sample;

reporting means reporting the parameter of the blood sample; and a sample handler comprising:

a sampler bed receiving a blood sampler which contains the blood sample and a stirring element, and moving means moving the stirring element in the sampler when the sampler is arranged in the sampler bed.

Compared to the traditional handling and analysis of blood samples for blood analysis, the blood analyzer according to this aspect of the invention provides efficient stirring and in turn blood sample homogeneity.

Sample stirring by means of moving a stirring element in a container is known in the technical field of injection as well, e.g. as disclosed in International Patent Application WO 00/12157. WO 00/12157 discloses a syringe and injector for injection of ultrasound contrast agents and which incorporate magnetic fluid agitation devices. An agitation element is disposed within the body of the syringe and is acted on by a magnetic field generated by an automatic source associated with the syringe. A plunger is movably disposed within the syringe body to be moved forward for injection of the contrast agent. WO 00/12157, however, does not address the specific demands for handling of blood samples, nor does it address the problem of integrated sample handling and analysis.

As used herein, the term "blood analyzer" means a device for handling and analysis of blood samples for determination of one or more parameters thereof. In this context, handling may comprise e.g. receiving, stirring, cooling, and positioning of blood samples.

As used herein, the term "control system" means a unit for controlling the operation of the analyzer. The control system may comprise hardware and software for operating e.g. the moving means, the exposure means, and the reporting means of the analyzer. The control system may be a built-in personal computer.

As used herein, the term "parameter" means any piece of clinical information about the blood sample, in particular: pH, concentrations of electrolytes, such as $Li^+$, $Na^+$, $K^+$, $Ca^{2+}$, $Mg^{2+}$, $Cl^-$, $HCO_3^-$, and $NH_3$ ($NH_4^+$), concentrations of dissolved gases, such as oxygen and carbon dioxide (conventionally reported in the form of partial pressures, e.g. $PO_2$, $pCO_2$), hematocrit (Hct), concentration of hemoglobin (ctHb) and hemoglobin derivatives, such as oxyhemoglobin, deoxyhemoglobin, methemoglobin, carboxyhemoglobin, sulfhemoglobin and fetal hemoglobin, and concentrations of metabolic factors, such as glucose, creatinine, urea (BUN), uric-acid, lactic acid, and bilirubin.

As used herein, the term "sensor" means any kind of organ, which is capable of:

selectively interacting with the chemical species of interest, thereby producing a well-defined and measurable response which is a function of the desired characteristic of that chemical species, the desired characteristic thus being derivable therefrom, or of responding to a bulk property of blood, the response not being selective with respect to any specific chemical species, but being a function of the total concentration of one or more chemical species in the blood, the desired characteristic thus being derivable therefrom.

In particular, the sensors of the blood analyzer of the present invention may be electrochemical sensors like potentiometric or amperometric sensors, or they may be optical sensors.

As used herein, the "exposure means" may e.g. comprise inlet means for introducing a test sample to a sensor section of the blood analyzer. The "exposure means" may comprise an inlet probe for aspirating the test sample. The inlet means or the inlet probe may be in fluid tight communication with a conduit. The conduit may comprise measuring chambers. It is preferably a tubing or a channel providing a fluid tight path for transport of blood through the conduit. The blood may be transported through the conduit by means of a pump. The sensor may thus be exposed to the blood, either directly in the conduit or in a measuring chamber. The exposure of the sensor to the blood may be a direct physical contact between the sensing surface and the blood or it may be an indirect contact, the wall of the conduit or the measuring chamber separating the sensing surface from the test fluid.

Alternatively, the blood sample may be exposed to analysis while remaining in the blood sampler, e.g. by optical means. Thus, the blood sampler holding the blood sample may be exposed to light of one or more appropriate wavelengths and the response from the sample measured.

As used herein, the term "reporting means" may comprise a printer, a display or interface capable of communicating or taking part in the communication of the parameter to the operator.

As used herein, the term "sample handler" means a device for handling blood samples. Handling may comprise receiving, stirring, cooling, and positioning of blood samples in blood samplers, and the sample handler may have specific means therefor. The sample handler may further have identification means for identification of blood samplers holding specific blood samples, e.g. bar code reading means for reading sampler bar codes.

As used herein, the term "sampler bed" means a support onto or into which a sampler may be placed when arranged in the sample handler. The sampler bed may e.g. be a recess for receiving a blood sampler. The sampler bed may be horizontal, angled, or vertical, and the sampler may be arranged accordingly therein.

As used herein, the term "blood sampler" means a device for collection of blood such as a syringe, a capillary tube, or a test tube, e.g. a vacuum test tube or a similar device designed for blood sampling.

As used herein, the term "stirring element" means a body which, when physically moved within the volume of a blood sample, provides stirring thereof. The stirring element may be e.g. a spherical element or a cylindrical element with rounded ends.

As used herein, the term "moving means" means a mechanical, gravitational, electrical, magnetic, or any other physical means which acts on the stirring element, thereby forcing the stirring element to move relative to the blood sampler in which it is arranged. Thus, it may be e.g. a tilting or rotating surface or it may be a magnetic arrangement in which a magnet acts on a magnetic stirring element.

The sample handler may be a separate unit of the blood analyzer or it may be integral with the analyzer. Upon integration of the sample handler with the blood analyzer, handling and analysis of blood samples are facilitated as compact, easy-to-handle instruments are obtained.

The moving means moving the stirring element may be a mechanical means. Thus, the moving means may be a robot arm or a support for moving, e.g. tilting or rotating, the sample handler and/or the sampler bed, thereby moving the stirring element held in any sampler therein by means of gravitational forces.

It should be understood, that the movement of the stirring element is the movement relative to the sampler. Such relative movement may be a movement of the stirring element relative to a stationary blood sampler. It may as well be the movement of the sampler relative to a stationary stirring element. Alternatively, both of the blood sampler and the stirring element may be moved, including a relative movement between the sampler and the element.

The moving means for moving the stirring element may also be an inlet probe of the blood analyzer. Thus, according to this embodiment, the movement of the stirring element may be provided by a movement of the inlet probe within the blood sample in the sampler. By mechanically or magnetically coupling the inlet probe to the stirring element, the stirring element may be moved with the inlet probe. The coupling may be accomplished by means of a holding and release mechanism by which the stirring element during stirring is held by the inlet probe, and, upon completion of the stirring, is released.

Preferably, however, the interaction between the stirring element and the moving means is magnetic. Thus, according to a preferred embodiment of the invention the stirring element is a magnetic element and the moving means is a magnet.

Magnetic interaction between the moving means and the stirring element provides strong interaction, which in turn provides high degree of freedom in the design of the blood analyzer.

As used herein, the term "magnetic element" means an element, which is susceptible to a magnetic field. Thus, the magnetic element may have a permanent magnetic moment or an induced moment due to the influence of a magnetic field. Accordingly, the magnetic element may comprise a permanent magnet or a magnetizable element like stainless steel.

As used herein, the term "magnet" means an element which has a magnetic field. Thus, the magnet may be a permanent magnet, i.e. an element which has a permanent magnetic field or it may be an electromagnet, i.e. an element which has a magnetic field when acted upon by an electric current. The magnet may comprise an iron, nickel, or cobalt containing substance, e.g. the magnet may be a neodymium-iron-boron permanent magnet.

The stirring element may e.g. be a permanent magnet or a magnetizable element. The stirring element may be a polymer body in which magnetic particles are embedded. Thus, the stirring element may be e.g. a polypropylene body with embedded particles of ferritic stainless steel.

By moving either of the magnet of the moving means or the magnetic stirring element, the magnetic field acting on the stirring element changes. Upon such changes of action, the stirring element may move accordingly within the sampler.

The stirring element is preferably a permanent magnet. As a permanent magnet has a magnetic field in itself, the interaction between a permanent magnet stirring element and the moving means is stronger than between a magnetizable stirring element and the moving means. The stronger interaction provides higher degree of design freedom, as the moving means may be placed further away from the sampler while still providing sufficiently strong interaction to move the stirring element. The stirring element may be a neodymium-iron-boron permanent magnet.

According to a preferred embodiment of the invention, the moving means moves the stirring element linearly within the blood sampler. The linear movement provides efficient stirring of blood samples in blood samplers, in particular in blood sampler having a longitudinal axis.

As used herein, the term "linearly" means that the stirring element is moved one-dimensionally within of the sampler. Preferably, the stirring element is moved along a longitudinal axis of the blood sample to provide stirring in the whole length thereof.

The linear movement of the stirring element may be accomplished by the linear movement of a magnet along the sampler. Thus, the moving means herefor preferably comprises a linear guide arranged adjacent to the sampler and more preferably in parallel to the longitudinal axis thereof. A magnet is arranged in a support of the linear guide such that the lines of, magnetic flux from the magnet extend perpendicular to the sampler. Upon displacing the support back and forth, preferably along the longitudinal axis of the sampler, the magnet is moved, and in turn the stirring element is moved linearly within the sampler, thereby stirring the blood sample.

According to another preferred embodiment of the invention, the moving means rotates the stirring element.

As used herein, the term "rotates" means that the stirring element is moved around an axis or a point within or outside the element. Stirring by means of rotation provides efficient stirring of the blood sample due to the turbulence created therein.

The rotation of the stirring element may be accomplished by rotation of a magnet arranged adjacent to the sampler. The magnet is preferably arranged such that the lines of magnetic flux from the magnet extend parallel to the sampler. Upon rotation, the magnet and in turn the stirring element are rotated.

The moving means herefor may comprise a rotor in which the magnet is arranged adjacent to the sampler. As further used herein "rotor" means a mechanical rotating entity having a center axis and which may hold a body at the center axis or in a distance therefrom. Upon rotation of the rotor, the body is rotated around this axis.

According to a further preferred embodiment of the invention, the rotation of the stirring element may be combined with a linear movement thereof. Thus, the moving means may be combined as well, e.g. that a rotor holding a magnet may be arranged in the support of a linear guide. By rotating the rotor and shifting the support back and forth, the stirring element rotates and moves linearly.

According to another preferred embodiment of the invention, the moving means moves the stirring element elliptically within the blood sampler.

As used herein, the term "elliptically" means that the stirring element is simultaneously moved longitudinally and transversely within the sampler. The transverse movement may include a rocking along a curved inner surface of the sampler.

The elliptical movement of the stirring element provides particularly efficient blood sample stirring as a high fraction of the complete sample volume is stirred in each longitudinal stroke of the stirring element.

The elliptical movement of the stirring element is preferably accomplished by rotating a magnet in a distance from a center axis. Accordingly, the moving means herefor comprises a carrousel holding a magnet. By rotating the carrousel with the magnet, the stirring element describes an elliptical movement within the sampler. The magnet is preferably arranged in the carrousel such that the lines of magnetic flux from the magnet extend perpendicular to the sampler.

As used herein, the term "carrousel" means a mechanical rotating entity having a center axis and which may hold a body in a distance therefrom. Thus, upon rotation of the carrousel, the body is turned around the axis in the distance therefrom. It should be understood, that a carrousel is a particular embodiment of a rotor.

According to a preferred embodiment of the invention, another elliptical movement may be accomplished by a moving means in which a rotating carrousel holding a magnet is arranged in a support of a linear guide, which may be moved in parallel to the longitudinal axis of the sampler. The corresponding movement of the stirring element provides stirring in the whole length of the sampler.

When the analyzer comprises an inlet probe to be introduced into the sampler, the stirring element should be sufficiently large to allow proper stirring of the blood sample, however, it should allow the unhindered penetration of the inlet probe into the blood sampler for transfer of a test sample.

Thus, according to a preferred embodiment of the invention, the sampler has an inner diameter and a free height for a stirring element at rest in the sampler, and the ratio between said free height and said inner diameter is at most 0.5, preferably at most 0.4.

As used herein, the "free height for a stirring element at rest in the sampler" means the allowable height of the stirring element from the inside bottom of the sampler when the element is resting within the sampler. It should be understood, that the allowable height includes the height of the stirring element in itself when at rest as well as any slip between the resting element and the inside bottom of the sampler.

In those cases where the above ratio is at most 0.5, sufficient room is left for unhindered inlet probe penetration.

When a stirring element is present in the blood sampler at the point of sampling, air segments may be caught at the surface of the stirring element. In order to avoid entrapment of any such air segments in the sampler, the stirring element is preferably spherical. It has been found, that compared to e.g. sharp-edged stirring elements, spherically shaped stirring elements has little tendency to entrap any air segment, probably due to reduced edge effects.

According to an alternative preferred embodiment of the invention, the stirring element is oblong. As used herein, the term "oblong" means that the element has one dimension which is longer than any other dimension of the element. The oblong stirring element provides excellent stirring properties, e.g. by rotation thereof.

According to another preferred embodiment of the invention, the stirring element has rounded ends. As used herein, the term "rounded ends" means that the ends of the stirring element are rounded, i.e that they have no sharp edges. Thus, the rounded ends my be spherical or elliptical or have any other rounded shape. It has been found, that e.g. a cylindrical stirring element with spherical ends provides excellent stirring properties and little tendency of air segment retention.

According to a further preferred embodiment of the invention, the stirring element is an ellipsoid or a superellipsoid. As used herein, the term "ellipsoid" is an ellipsoid of revolution or a spheroid. The term "superellipsoid" means a superellipsoid of revolution or a superspheroid. It has been found, that air segment entrapment may as well be avoided, using elliptical stirring elements, which also provide excellent sample stirring properties.

According to still another further preferred embodiment of the invention, the stirring element may be an oblong element having edged ends with no sharp angles between joining surfaces. Thus, the stirring element may e.g. be a hexagonal element with six-edged ends in which all angles between joining surfaces at the elements ends are obtuse, e.g. at least 100°.

According to a preferred embodiment of the invention, the oblong stirring element has a longitudinal axis and end points and the moving means rotates the stirring element so that the longitudinal axis thereof rotates around an end point of the stirring element.

As used herein, the term "the longitudinal axis rotates around an end point" means the stirring element is rotated so that at first its longitudinal axis is rotated by half a rotation about the first end point of the stirring element. Subsequently, the longitudinal axis is rotated by half a rotation around the second end point of the element. Optionally, these steps are repeated. It should be understood that in this context the term "end point" comprises the exact end points as well points at the surface of the element in some distance from the exact end point. Thus, in the case of the oblong stirring element being rod-shaped, the rotation is in fact around the exact end point. In those cases, however, where the oblong stirring element is e.g. elliptical, the rotation is a rotation around the exact end point and points at the surface of the element in some distance from the exact end point.

According to the "waddling" movement pattern of the stirring element the sample is stirred excellently.

The "waddling" may be accomplished by moving a magnet along the sampler, preferably along the longitudinal axis thereof. It should be understood, that in order to perform such "waddling", the friction between the stirring element and the sampler wall should be sufficient to prevent the stirring element from "skidding" along the sampler wall without "waddling". Accordingly, the stirring element has preferably a friction surface, e.g. in terms of a patterned or sanded surface or in terms of a surface coating, e.g. a polymer coating. Due to the friction and polarization of the stirring element when acted on by moving the magnet, the "waddling" movement pattern of the stirring element is obtained.

The moving means herefor may comprise a linear guide arranged along the sampler and preferably in parallel to the longitudinal axis thereof. A magnet is arranged in a support of the linear guide such that the lines of magnetic flux from the magnet extend perpendicular to the sampler. Upon displacing the support back and forth along the sampler, the magnet is moved, and in turn the stirring element is moved linearly within the sampler, thereby stirring the blood sample.

It should be understood, that the invention covers any other combination of the above components beyond those specifically described, i.e. any parallel, perpendicular or inclined arrangement of the magnet, any combination of magnet or magnetizable materials as well as any combination of the above movement patterns of the stirring element.

According to still another preferred embodiment of the invention, the sampler bed has a guide facilitating blood sampler positioning in the sampler bed. The guide may facilitate alignment of the blood sampler in the sampler bed, and in turn facilitate exposure of the blood sample to the sensor of the blood analyzer. The guide may be a recess or a socket supporting the sampler, or it may be a set of ribs aligning the sampler. The sampler may have corresponding means for fitting with the guide.

According to still another preferred embodiment of the invention, the sample handler comprises additional sampler beds. Preferably, the sample handler comprises two to five sampler beds. A plurality of sampler beds may allow the handling and analysis of a plurality of blood samples held in blood samplers. In such case one blood sample may be analyzed while other blood samples are automatically maintained, and, upon completing of the analysis of the one blood sample, in turn be analyzed.

Preferably, the sample handler comprises additional moving means for moving stirring elements in blood samplers arranged in the additional sampler beds. Where the blood sample handler has a plurality of sampler beds, the means for moving the stirring element may be a means for moving one stirring element at a time or simultaneously moving the stirring elements in each of the samplers. Accordingly, the elements may be moved in any combination or alone, e.g. one element out of five, two out of five, three out of five, four out of five, or all five elements, e.g. depending on the number of blood samplers in the handier and the stirring demand for each sampler.

According to still another preferred embodiment of the invention, the blood analyzer comprises an inlet probe and the inlet probe and the sampler bed are movable relative to each other to provide fluid communication between the inlet probe and a blood sampler arranged in the sampler bed. Thus, a test sample may be transferred from the blood sampler to the inlet probe, from which it may in turn be transferred via a conduit system to a sensor section of the analyzer, comprising one or more sensors. The inlet probe is preferably an aspiration inlet tube. The means for moving the inlet probe relative to the sampler bed may be a means for moving the inlet probe relative to a stationary sample handler, or it may be a means for moving one or more sampler beds relative to a stationary inlet probe.

A sample handler comprising a plurality of sampler beds may have these beds arranged in a parallel arrangement or in a radial arrangement. Accordingly, the inlet probe may move linearly or rotate, respectively, between positions corresponding to each bed in order to approach a blood sampler arranged therein.

According to a preferred embodiment of the invention, the means for moving the inlet probe may be an electric motor, which, via a gear, provides the movement of the inlet probe. Likewise, the means for moving the sampler bed may be an electric motor, which, via a gear, provides the movement of the sample bed.

According to another preferred embodiment of the invention, the inlet probe may be placed in an auxiliary inlet probe position from which the inlet probe may collect a sample from a sampler arranged in an auxiliary sampler position. It should be understood, that the auxiliary inlet probe position is an additional inlet probe position to which there is no corresponding sampler bed in the sample handler. The auxiliary sampler position is a separate sampler position arranged adjacent to the sample handler. The combination of the auxiliary inlet probe position and the auxiliary sampler position makes up an "emergency inlet", which may be used for immediate transfer of a test sample from the sampler. A sampler is typically handheld in the auxiliary sampler position and is not stirred in this position.

According to another preferred embodiment of the invention, the blood analyzer has a display adapted to report any status and identification data of the currently analyzed sample, of the current analysis, and of the current collection sequence. The display preferably comprises a touch screen for operating the analyzer. Thus, the desired mode of analysis, collection sequence, stirring pattern, etc. may be selected via the touch screen.

According to a preferred embodiment of the invention, sampler beds may be adapted for receiving particular types of blood samplers. Thus, for reception of syringes, the sampler beds are preferably inclined by an angle in the range 10–30° relative to horizontal. The inclined arrangement of syringes facilitates the accumulation of any air segment left in the syringe as well as the collection of the full syringe volume. Further, syringes are less likely to leak when arranged inclined. Capillary tubes, on the other hand, are less likely to leak when arranged horizontally, and thus capillary tubes are preferably arranged in sampler beds which are horizontally positioned.

According to a preferred embodiment of the invention, the sample handler comprises a cooling element, preferably a Peltier-element, situated adjacent to the sampler bed for cooling a blood sample arranged in the sampler bed.

The sample handler preferably has an identification means for identification of a blood sampler arranged in the sampler bed. The identification means may have a reading means for reading identification data stored in a sampler memory means, e.g. a bar code reader for reading a sample identification bar code on the blood sampler.

According to a second aspect of the invention, a method for handling and analyzing a blood sample contained in a blood sampler with a stirring element is provided, said method comprising the steps of:

arranging the blood sampler in a sampler bed in a sample handler of a blood analyzer;

stirring the blood sample by moving the stirring element in the sampler;

exposing the sensor to the blood sample;

measuring a parameter of the blood sample; and reporting the parameter.

Compared to traditional handling and analysis of blood samples for blood analysis, the method according to this aspect of the invention has the advantage that it provides efficient stirring and in turn blood sample homogeneity.

It should be understood, that with the method the operator may leave the blood sampler with the blood analyzer for automatic maintenance. Thus, the operator need not manually maintain the blood sample up to the point of analysis.

It should further be understood, that according to the method of the present invention a sample may be left for as long as thirty minutes with the blood analyzer while still allowing correct analytical results to be obtained.

According to this second aspect of the invention, a plurality of blood samples may be exposed to the sensor for analysis according to a predetermined exposure sequence. Examples of such exposure sequences are:

(a) a chronological sequence according to which the time of receipt of a blood sampler in the sample handler is recorded and in which the exposure sequence is a chronologically ordered sequence, so that at any time the oldest received sample is exposed;

(b) an alternative chronological sequence wherein the time of sampling from the patient is recorded and in which the exposure sequence is a chronologically ordered sequence, so that at any time the oldest sample is exposed;

(c) a numerical sequence wherein the sampler beds are numbered, in which the samplers are numbered in accordance hereto, and in which the exposure sequence is a numerically ordered sequence, i.e. a blood sample from the lowest numbered sampler is exposed and then from the next lowest numbered sampler etc. Subsequent to exposure of a blood sample from the highest numbered sampler, the sequence is repeated;

(d) a prioritized numerical sequence wherein the sampler beds are numbered, in which the samplers are numbered in accordance hereto and in which the exposure sequence is so ordered that at any time a blood sample is exposed from the sampler with the lowest number;

(e) a "rejection" sequence wherein the time of receipt of the samplers in the sample handler or the time of sampling is recorded, and in which samplers from which blood samples have not been exposed within a predetermined time range from the time of receipt or of sampling, are rejected;

(f) a "non-rejection" sequence wherein the time of receipt of a sampler in the sample handler is recorded and in which samplers from which a blood sample has not exposed within a predetermined time after the time of receipt are prioritized; and (g) an alternative "non-rejection" sequence wherein the time of sampling from the patient is recorded and in which samplers from which blood samples have not been exposed within a predetermined time after the time of sampling are prioritized.

The completion of sample analysis may be displayed to inform the operator that the sampler may be removed. An alarm may be activated in case a sampler is removed before a test sample therefrom has been analyzed, e.g. as sensed by a sensor in the sampler bed.

According to a preferred embodiment of this aspect of the invention, the blood analyzer has an inlet probe and the inlet probe and the blood sampler are moved into fluid communication with each other so as to allow transfer of a test sample from the blood sampler to the inlet probe. The inlet probe allow easy transfer of a test sample from the blood sampler for analysis.

According to a further preferred embodiment of this aspect of the invention, the test sample is transferred to the inlet probe from a plurality of positions within the blood sampler. Such transfer procedure further compensates possible sample inhomogeneity as a test sample is provided which represents the complete blood sample.

The test sample transfer may be performed from at least two static positions within the blood sample in the sampler, or it may be performed while continuously moving the inlet probe within the blood sample in the sampler. Preferably, the test sample is transferred from a high number of randomly chosen positions within the blood sample. As blood foam may have gathered at the top of the blood sampler, e.g. in the luer of a syringe, test sample is preferably not transferred from the top.

According to another further preferred embodiment of this aspect of the invention, the transfer of a test sample from the blood sampler to the inlet probe comprises:

first transferring blood from the blood sampler to the inlet probe;

returning an amount of the blood from the inlet probe to the blood sampler;

optionally repeating the above; and then transferring the test sample from the blood sampler to the inlet probe.

The flow of blood, e.g in the inlet probe, per se provides stirring. The main body of a blood segment displays laminar flow, which in itself stirs the blood due to variations in the flow velocity along the cross section of the segment. At the front and at the tail of the segment the flow is turbulent, additionally stirring the blood. According to this preferred embodiment of the invention, the flow distance is extended and the flow is reversed at least twice, both phenomena contributing to blood stirring.

According to a further preferred embodiment, the above transfer procedures are combined, thus shifting the position of the inlet probe while transferring and returning blood.

According to a third aspect of the invention, a blood sample handler is provided which comprises:

an interface providing operational communication with a blood analyzer, a sampler bed receiving a blood sampler which contains a blood sample and a stirring element, and moving means moving the stirring element in the sampler when the sampler is arranged in the sampler bed.

The sample handler may be a separate entity to be used with, and optionally integrated with, any blood analyzer. The sample handler provides maintenance of the blood sample up to the point of analysis, and upon connection of the sample handler with a blood analyzer sample handling and analysis are further facilitated. According to this aspect of the invention, the sample handler may be used with a variety of blood analyzers.

As used herein, the term "interface providing operational communication" means any interface of the blood sample handler towards the blood analyzer, which may be used for their mutual communication. Thus, the interface may comprise electronic connection means for electronic connection of the handler to the analyzer, e.g. for the handler to be controlled from the analyzer. The interface may as well comprise physical connection means for physically combining the handler to the analyzer, and it may comprise transfer means for allowing transfer of a test sample from a sampler held in the handler to the analyzer.

According to a preferred embodiment of this third aspect, the sampler bed is movable between separate positions in the sample handler. The movement of the sampler bed may position a blood sampler arranged therein for exposure to analysis or for transfer of a test sample therefrom, e.g. positioning the blood sampler relative to an inlet probe of a blood analyzer.

According a fourth aspect of the invention, a method for handling a blood sample contained in a blood sampler with a stirring element is provided, comprising the steps of:

arranging the blood sampler in a sampler bed in a sample handler; and stirring the blood sample by moving the stirring element in the sampler.

Compared to traditional handling and analysis of blood samples for blood analysis, the method according to this aspect of the invention has the advantage that it provides efficient stirring and in turn blood sample homogeneity.

In the following, preferred embodiments of the invention are described with reference to the figures.

FIG. 1 shows an embodiment of a blood analyzer (100) according to the invention. The blood analyzer (100) comprises a sample handler (110) with a sampler bed (120) holding a syringe (130) with a magnetizable stirring element (150). The function of the sample handler (110) is described in detail in connection with FIGS. 2–8. The blood analyzer (100) further comprises an inlet probe (270) for transfer of a test sample via an analyzer conduit (300) to a set of four sensors (310*a*–*d*) arranged in a sensor section (320). A soft touch screen display (290) is used for operation of the blood analyzer (100), including communication of analysis results to the operator.

Figure 2:
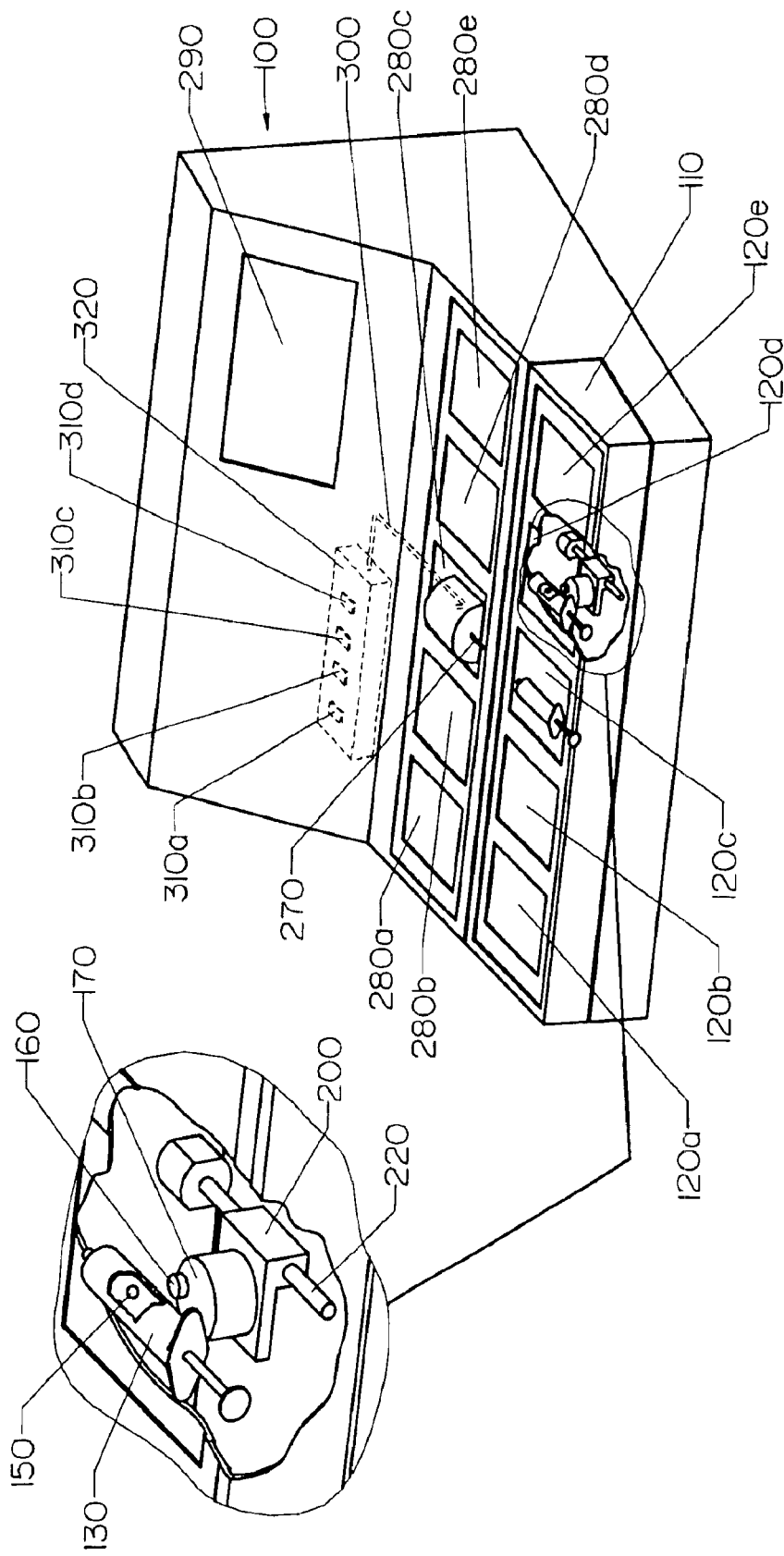
FIG. 2 shows another embodiment of a blood analyzer according to the present invention.

FIG. 2 shows a preferred embodiment of a blood analyzer (100) of the present invention. This analyzer corresponds to the analyzer (100) shown in FIG. 1, but comprises a sample handler (110) having five sampler beds (120*a*–*e*). Each of the five sampler beds (120*a*–*e*) may accommodate a syringe (130) holding a blood sample (not shown) and a magnetizable spherical stirring element (150).

The means for moving the stirring element (150) in the syringe (130) is a permanent magnet (160) situated below each of the sampler beds (120*a*–*e*). The permanent magnet (160) is arranged in carrousel (170), which in turn is rotated by an electric motor (not shown), connected to the carrousel (170) by a drive belt (not shown). The carrousel (170) is positioned on a support (200), which is linearly moved by an additional electric motor (not shown);, connected to the support (200) via a linear guide (220). The carrousel (170) may be rotated independently of the movement of the support (200), which in turn may be moved independently of the rotation of the carrousel (170). The moving means of each sampler bed may be operated independently. Thus, it should be understood, that the analyzer (100) may be operated with any number of the five sampler beds (120a–e) being occupied by blood samplers.

As can be seen from FIG. 2, the blood sample handler (110) is integral with the blood analyzer (100). The blood analyzer (100) is automatic and the operator may leave a blood sample with the analyzer for automatic maintenance and analysis.

The analyzer (100) has an inlet probe (270), which may be moved between five separate inlet probe positions (280a–e), each position corresponding to one of the five sampler beds (120a–e). The inlet probe (270) is an aspiration probe, which, when extended into the syringe (130), may aspirate a test sample for transfer via an analyzer conduit (300) to a set of four sensors (310a–d) arranged in a sensor section (320). The inlet probe has an additional inlet probe position (not shown) to which there is no corresponding sampler bed. This additional position may be used for urgent transfer of a test sample from a sampler not arranged in the sample handler.

A soft touch screen display (290) is used for operation of the blood analyzer (100).

The sample handler (110) has a Peltier-element (not shown) for cooling of blood samples held in the handler.

Figure 3:
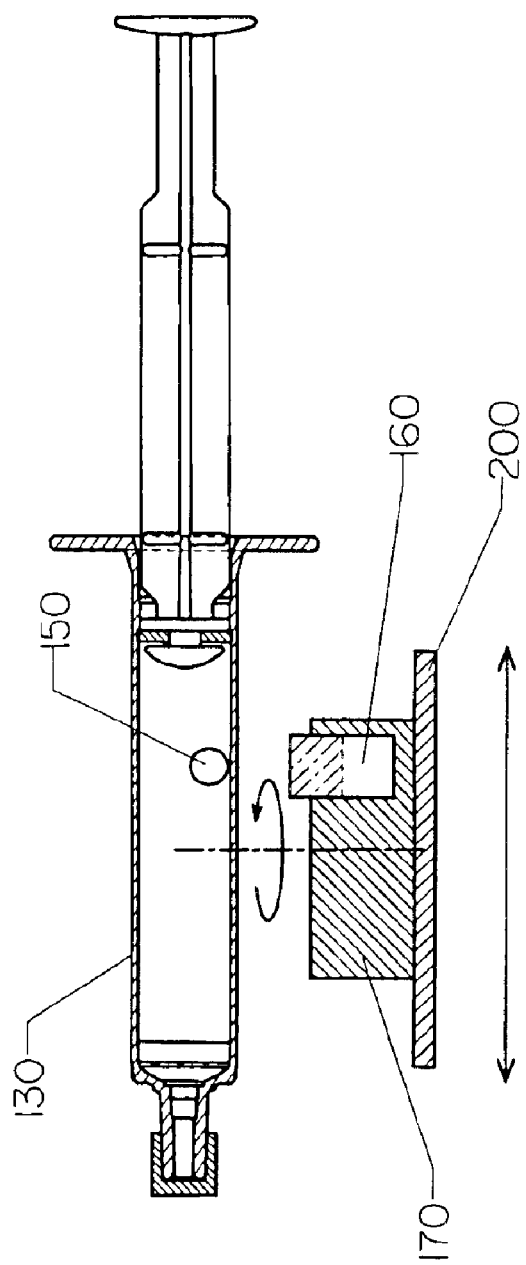
FIG. 3 is a schematic view of the sample handler of the analyzer of FIG. 2.

FIG. 3 shows the sample handler (110) of the blood analyzer of FIG. 1 and the stirring principle thereof.

The syringe (130) has an inner diameter of 10 mm and an active barrel length of 50 mm. The magnetizable stainless steel spherical stirring element (150) has an outer diameter of 3,5 mm, thus taking up 35% of the diameter of the syringe when at rest in the syringe (130).

The spherical stirring element (150) arranged in the syringe (130) is moved elliptically within the syringe (130). The elliptical movement pattern is obtained by the moving means (160, 170, 200).

The carrousel (170) has an outer diameter of 32 mm, and the cylindrical neodymium-iron-boron magnet (160) of a diameter of 8 mm is arranged in the carrousel (170), such that the center axis of magnet is in a radial distance of 9 mm from the carrousel center. The carrousel (170) is arranged below the syringe (130), such that the distance between the top of magnet (160) and the bottom of the syringe is 3 mm. The magnet (160) is arranged vertically in the carrousel such that the lines of magnetic flux of from the magnet (160) extend perpendicular to the syringe (130).

The carrousel (170) is positioned on a support (200), which is displaceable parallel to the syringe (130). The maximum length of stroke of the support (200) is 70 mm. The carrousel (170) is rotated at a frequency of 700 rounds per minute, and the support (200) is moved at a rate of sixteen strokes per minutes at a length of stroke of 12 mm. Due to the rotation of the carrousel (170), the stirring element (150) is moved elliptically in the syringe (130). Thus, the stirring element (150) sweeps one side of the blood sample volume during the first leg of a longitudinal stroke, whereas the other side of the sample volume is swept during the second leg of the longitudinal stroke. Accordingly, the blood sample is excellently stirred.

It should be understood that in order to stir the complete volume of the blood sample held in the syringe (130), the sum of twice the radial distance of the magnet (160) in the carrousel (170), the magnet diameter, and the length of stroke of the support (200) should make up at least 60% of the active barrel length of the syringe (130). Due to the turbulent flow field arising around the stirring element, however, the sum needs not make up the full 100% of the active barrel length of the syringe (130).

Figure 4:
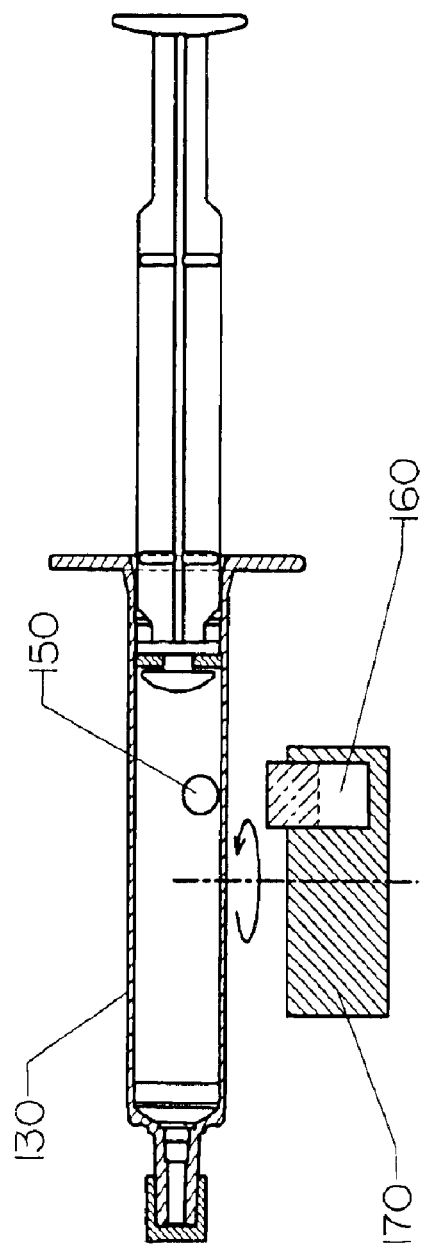
FIG. 4 is a schematic view of a second embodiment of a sample handler.

FIG. 4 is a schematic view of an alternative embodiment of a sample handler in which the moving means also moves the stirring element (150) elliptically within the syringe (130).

The moving means of the sample handler of FIG. 4 is similar to the moving means (160, 170) of the sample handler of FIGS. 2 and 3, however, without the support (200). The carrousel (170) is rotated at a frequency of 700 rounds per minute, thereby moving the stirring element (150) elliptically within the syringe (130) and stirring the blood sample.

Compared to the sample handler of FIG. 3, the sample handler of FIG. 4 has a simpler construction. The sample handler of FIG. 3 provides better stirring than the sample handler of FIG. 4; however, the latter may still be used for blood samples, which require only minor stirring.

Figure 5:
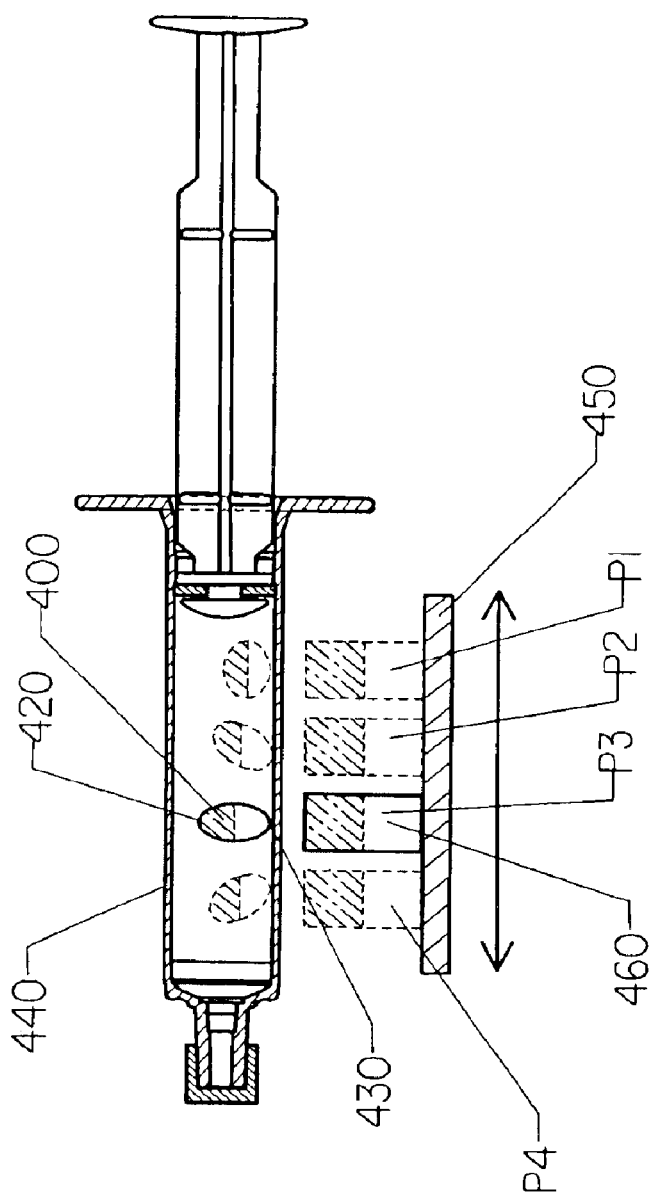
FIG. 5 is a schematic view of a third embodiment of a sample handler.

FIG. 5 shows the stirring: principle according to an alternative embodiment of the invention in which the stirring element "waddles".

An ellipsoid-shaped magnetizable stainless steel stirring element (400) has a longitudinal axis of 7 mm and two mutually perpendicular transverse axes of 3.5 mm, both of these transverse axes being perpendicular to the longitudinal axis. The element (400) has a sanded surface and is arranged in a blood sample-holding syringe (440). The syringe (440) has an inner diameter of 10 mm and an active barrel length of 50 mm.

The moving means comprises a linearly movable support (450) of a maximum length of stroke of 70 mm, arranged in parallel to the longitudinal axis of the syringe (440). A cylindrical neodymium-iron-boron magnet (460) is arranged horizontally in the support (450) at a distance of 3 mm below the syringe (440), such that the lines of magnetic flux from the magnet (460) extend perpendicular to the syringe (440).

The linear guide (450) is moved at a rate of eighty strokes per minutes at a length of stroke of 42 mm. The stirring element (400) "waddles" along the longitudinal axis of the syringe (440). The "waddling" includes a first rotation by half a turn of the longitudinal axis of the stirring element around a first end point (420) of the stirring element, followed by a second rotation by half a turn of the longitudinal axis around a second end point (430) of the stirring element. It should be understood that with an elliptical stirring element, an "end point" comprises the exact end point and points at the surface of the element in some distance from the exact end points.

Four positions P1–P4 of the magnet (460) and in turn the stirring element (400) is shown in FIG. 5. In position P1, the element (400) is at rest. Upon being moved to positions P2 and P3, the element (400) is rotated around its second end point (430), until it reaches its upright position (P3). As can be seen from FIG. 5, the magnetic polarisation of the stirring element is gradually changed between the positions P1–P4. The gradual change of polarisation, along with the frictional sanded surface preventing the stirring element from "skidding", are essential for the "waddling". In position P4, the "waddling" from P1–P3 is continued along the longitudinal axis of the syringe (440).

Due to the irregularity of the "waddling" movement pattern the blood sample is stirred excellently.

It should be understood that in position P1, at rest, the stirring element (400) takes up 35% of the syringe diameter, thus leaving sufficient room for penetration of an inlet probe into the syringe (440). During rotation, the upright position (P3) is reached, in which the stirring element (400) takes up 70% of the syringe diameter. This upright position (P3), however, is not stable, and upon completion of the stirring, the element (400) will tend to lay on its largest surface, corresponding to position P1, allowing unhindered inlet probe penetration.

Figure 6:
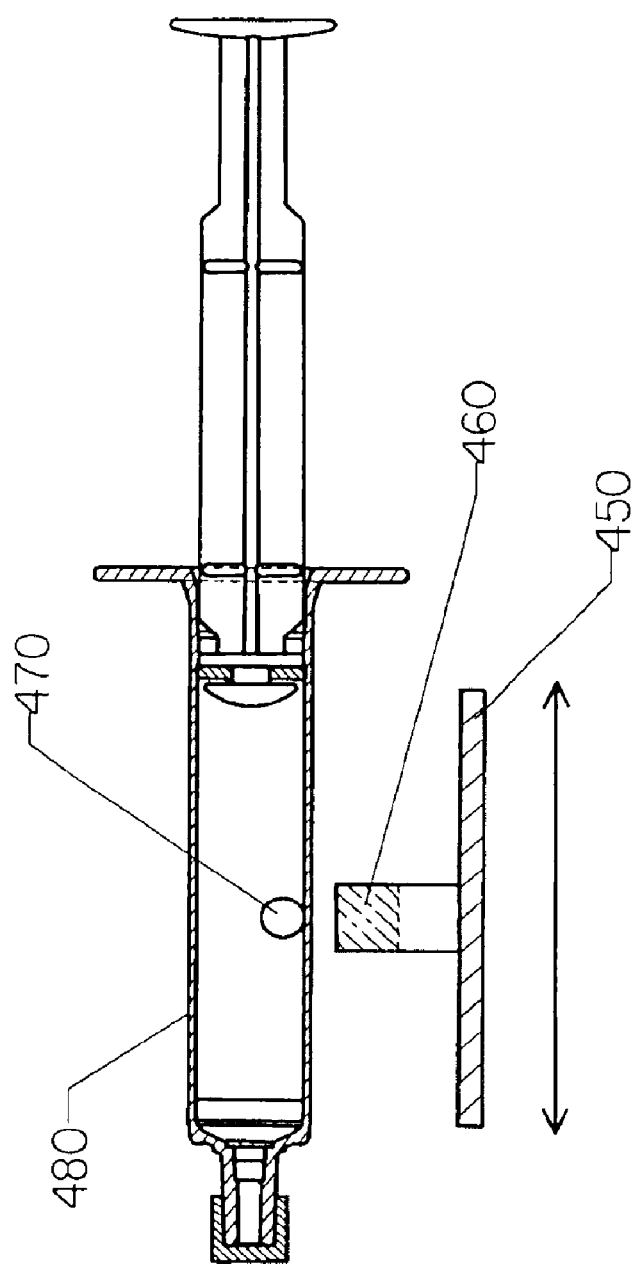
FIG. 6 is a schematic view of a fourth embodiment of a sample handler.

FIG. 6 shows the stirring principle according to a further alternative embodiment of the invention in which the moving means moves the stirring element linearly within the blood sampler.

A stainless steel magnetizable spherical stirring element (470) having a diameter of 5 mm is arranged in a blood sample-holding syringe (480). The syringe (480) has an inner diameter of 10 mm and an active barrel length of 50 mm.

The moving means used for the linearly moving of the spherical stirring element (470) is the same as used in FIG. 5. The support (450) is moved at a rate of 100 strokes per minutes at a length of stroke of 42 mm. Accordingly, the magnet (460) is moved linearly along the longitudinal axis of the syringe (480) and in turn the stirring element (470) is moved linearly, stirring the blood sample. The stirring element (470) has a smooth surface reducing the frictional forces between the stirring element (470) and the blood sample and sampler, and in turn allowing the linear movement of the stirring element (470). It should be understood, that the spherical stirring element may roll in case it has a frictional surface.

Figure 7:
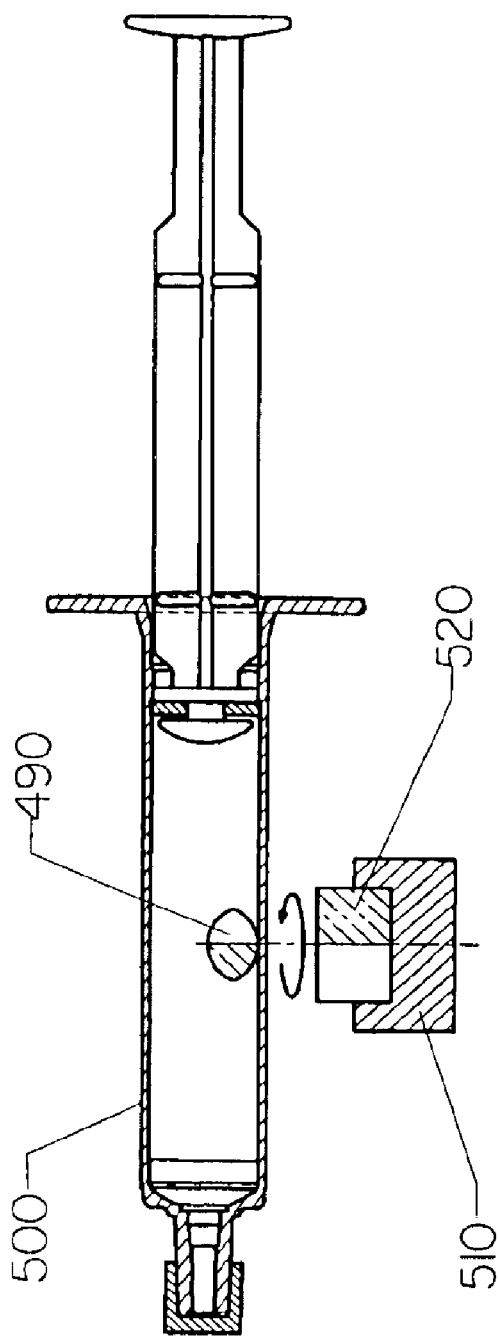
FIG. 7 is a schematic view of a fifth embodiment of a sample handler.

FIG. 7 shows the stirring principle according to yet another embodiment of the invention in which the stirring element rotates.

An ellipsoid-shaped neodymium-iron-boron permanent magnet stirring element (490) is arranged in a blood sample-holding syringe (500). The magnetizable ellipsoid-shaped stirring element (490) has a longitudinal axis of 7 mm and two mutually perpendicular transverse axes of 3.5 mm, both of these transverse axes being perpendicular to the longitudinal axis. The syringe (500) has an inner diameter of 10 mm and an active barrel length of 50 mm.

The moving means comprises a rotor (510) at the center of which a neodymium-iron-boron tubular magnet (520) is arranged, 3 mm below the syringe (500). The magnet (520) is arranged in the rotor (510) such that the lines of magnetic flux from the magnet (520) extend parallel to the longitudinal axis of the syringe (500).

The rotor (510) with the magnet is rotated at a frequency of 1000 rounds per minute, thereby rotating the stirring element (490), which in turn stirs the blood sample.

Compared to the sample handlers of FIGS. 1–3 and 5–6, the sample handler of FIG. 7 has a simpler construction. The sample handlers of FIGS. 1–3 and 5–6 provides better stirring than the sample handler of FIG. 7, however, the latter may still be used for blood samples, which require only minor stirring.

Figure 8:
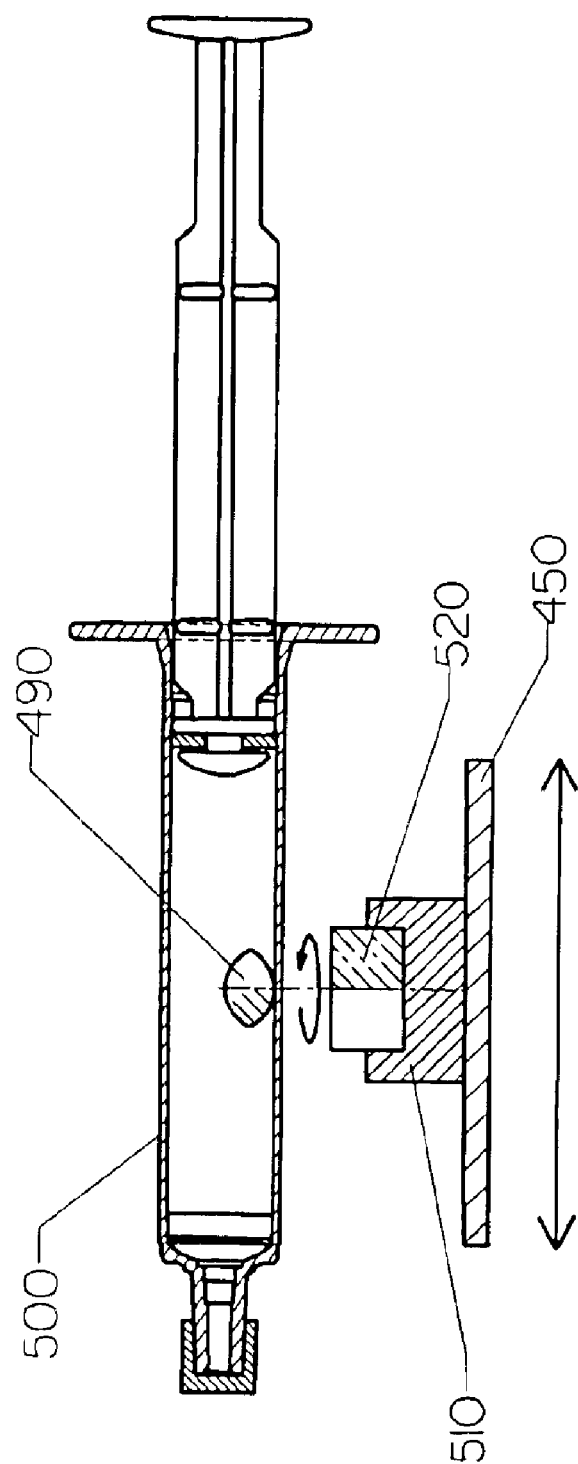
FIG. 8 is a schematic view of a sixth embodiment of a sample handler.

FIG. 8 is a schematic view of a sample handler in which the moving means both rotates the stirring element and moves the stirring element linearly within the blood sampler.

The moving means of the sampler handler of FIG. 8 comprises the combined moving means of the sample handlers of FIGS. 6 and 7. Thus, it comprises a rotor (510) with a magnet (520) arranged in a support (450). The syringe and the stirring element correspond to the syringe (500) and the stirring element (490) of FIG. 7.

The rotor (510) is rotated at a frequency of 1000 rounds per minute, and the linear guide (450) is moved at a rate of sixteen strokes per minutes at a length of stroke of 42 mm. Thereby, the stirring element (490) is rotated and moved linearly within the syringe (500), and stirs the blood sample.

Due to the combined rotational and linear movement of the stirring element, the blood sample is stirred excellently.

It should be emphasized, that the scope invention is not limited to those embodiments described with FIGS. 1–8, which, however, are preferred embodiments of the invention.

The invention being thus described, it will be obvious that the same may be varied in many ways. Such variations are not to be regarded as a departure from the spirit and scope of the invention and all such modifications are intended to be included within the scope of the following claims.

What is claimed is:

1. A blood analyzer comprising:
   a control system controlling the operation of the analyzer;
   a sensor measuring a parameter of a blood sample;
   exposure means exposing the sensor to the blood sample, the exposure means comprising:
      an inlet probe;
   reporting means reporting the parameter of the blood sample; and
   a sample handler comprising:
      a sampler bed receiving a blood sampler which contains the blood sample and a stirring element, and
      moving means moving the stirring element in the blood sampler when the sampler is arranged in the sampler bed,
   in which the inlet probe and the sampler bed are movable relative to each other to provide fluid communication between the inlet probe and a blood sampler arranged in the sampler bed so as to allow transfer of a test sample from the blood sampler to the inlet probe.

2. The blood analyzer according to claim 1 in which the stirring element is a magnetic element and the moving means is a magnet.

3. The blood analyzer according to claim 1 in which the moving means moves the stirring element linearly within the blood sampler.

4. The blood analyzer according to claim 1 in which the moving means rotates the stirring element and moves the stirring element linearly within the blood sampler.

5. The blood analyzer according to claim 1 in which the moving means rotates the stirring element.

6. The blood analyzer according to claim 1 in which the moving means moves the stirring element elliptically within the blood sampler.

7. The blood analyzer according to claim 1 in which the sampler has an inner diameter and a free height for a stirring element at rest in the sampler, and in which the ratio between said free height and said inner diameter is at most 0.5.

8. The blood analyzer according to claim 1 in which the stirring element is spherical.

9. The blood analyzer according to claim 1 in which the stirring element is oblong.

10. The blood analyzer according to claim 9 in which the stirring element has rounded ends.

11. The blood analyzer according to claim 10 in which the stirring element is an ellipsoid or a superellipsoid.

12. The blood analyzer according to claim 9 in which the stirring element has a longitudinal axis and end points and in which the moving means rotates the stirring element so that the longitudinal axis thereof rotates around an end point of the stirring element.

13. The blood analyzer according to claim 1 in which the sampler bed has a guide facilitating blood sampler positioning in the sampler bed.

14. The blood analyzer according to claim 1 in which the sample handler comprises additional sampler beds.

15. A method for handling and analyzing a blood sample contained in a blood sampler with a stirring element comprising the steps of:

arranging the blood sampler in a sampler bed in a sample handler of a blood analyzer;

stirring the blood sample by moving the stirring element in the sampler;

exposing a sensor to the blood sample by moving an inlet probe of the blood analyzer and the blood sampler into fluid communication with each other so as to allow transfer of a test sample from the blood sampler to the inlet probe;

measuring a parameter of the blood sample; and reporting the parameter.

16. The method according to claim 15 in which the test sample is transferred to the inlet probe from a plurality of positions within the blood sampler.

17. The method according to claim 15 in which the transfer of a test sample from the blood sampler to the inlet probe comprises:

first transferring blood from the blood sampler to the inlet probe;

returning an amount of the blood from the inlet probe to the blood sampler;

optionally repeating the above; and then transferring the test sample from the blood sampler to the inlet probe.

18. A blood sample handler comprising:

an interface providing operational communication with a blood analyzer;

a sampler bed, which is movable between separate positions in the sample handler, receiving a blood sampler which contains a blood sample and a stirring element; and moving means moving the stirring element in the sampler when the sampler is arranged in the sampler bed.

19. The blood sample handler according to claim 18 in which the stirring element is a magnetic element and the moving means is a magnet.

20. The blood sample handler according to claim 18 in which the moving means rotates the stirring element and moves the stirring element linearly within the blood sampler.

21. The blood sample handler according to claim 18 in which the moving means moves the stirring element linearly within the blood sampler.

22. The blood sample handler according to claim 18 in which the moving means rotates the stirring element.

23. The blood sample handler according to claim 18 in which the moving means moves the stirring element elliptically within the blood sampler.

24. The blood sample handler according to claim 18 in which the sampler has an inner diameter and a free height for a stirring element at rest in the sampler, and in which the ratio between said free height and said inner diameter is at most 0.5.

25. The blood sample handler according to claim 18 in which the stirring element is spherical.

26. The blood sample handler according to claim 18 in which the stirring element is oblong.

27. The blood sample handler according to claim 26 in which the stirring element has rounded ends.

28. The blood sample handler according to claim 27 in which the stirring element is an ellipsoid or a superellipsoid.

29. The blood sample handler according to claim 26 in which the stirring element has a longitudinal axis and end points and in which the moving means rotates the stirring element so that the longitudinal axis thereof rotates around an end point of the stirring element.

30. The blood sample handler according to claim 18 in which the sample handler comprises additional sampler beds.

31. A method for handling a blood sample contained in a blood sampler with a stirring element comprising the steps of:

arranging the blood sampler in a sampler bed in a sample handler; and stirring the blood sample by moving the stirring element in the sampler, wherein the sampler bed is movable between separate positions in the sample handler.

* * * * *